United States Patent [19]

Molee et al.

[11] Patent Number: 4,773,905

[45] Date of Patent: Sep. 27, 1988

[54] WINGED NAPKIN HAVING CROSS-CHANNELING

[75] Inventors: Kenneth J. Molee, Spotswood; Kenneth B. Wilson, North Brunswick, both of N.J.

[73] Assignee: Personal Products Company, Milltown, N.J.

[21] Appl. No.: 90,174

[22] Filed: Aug. 27, 1987

[51] Int. Cl.⁴ .............................................. A61F 13/16
[52] U.S. Cl. ................................. 604/378; 604/385.1
[58] Field of Search ............... 604/386, 387, 378, 399, 604/385.1

[56] References Cited

U.S. PATENT DOCUMENTS 3,070,096 12/1962 Weitzman ........................... 604/399
4,285,343 8/1981 McNair ............................... 604/387
4,608,047 8/1986 Mattingly ........................... 604/387

Primary Examiner—John D. Yasko

[57] ABSTRACT

A sanitary napkin having flaps extending laterally from each of the longitudinal edges of its central absorbent element is provided with at least one fluid retarding channel disposed transversely across the absorbent element for inhibiting the transmission of body fluid from a central portion of the absorbent element to at least one transverse end. The preferred construction employs the use of two spaced apart compressed portions of the absorbent element to define a central absorbent portion and delay the transmission of body fluid from the central portion into the transverse end portions of the absorbent element, thereby minimizing the incidence of leakage from the ends of the napkin.

20 Claims, 2 Drawing Sheets

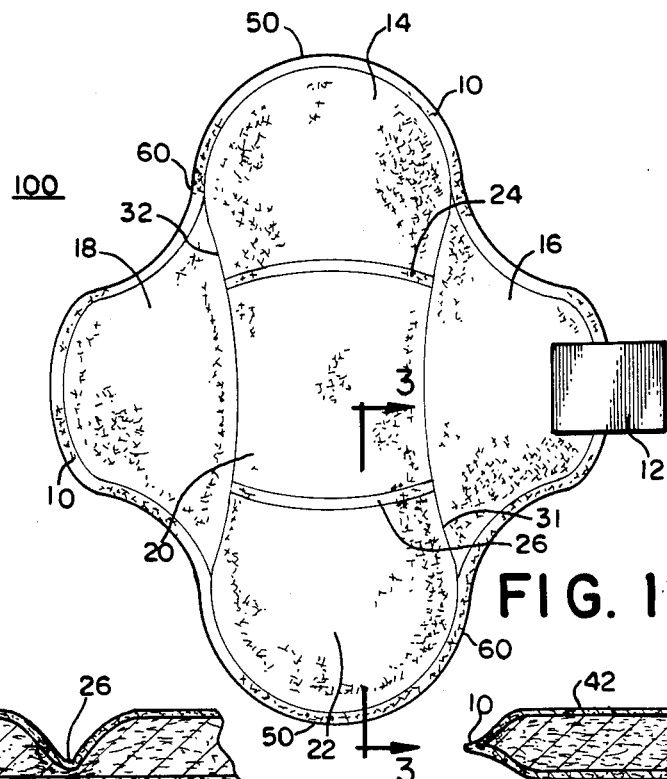
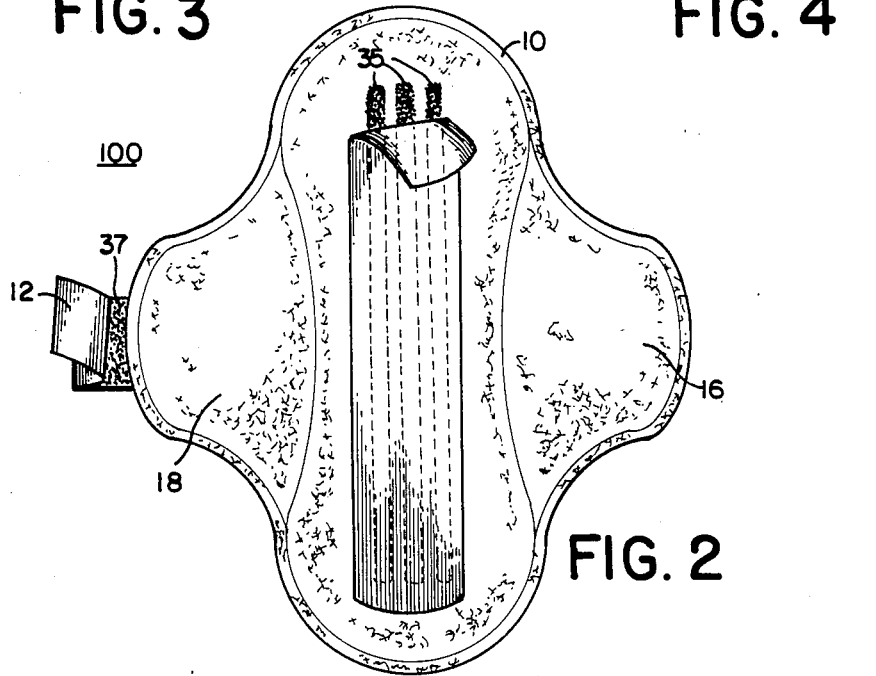

WINGED NAPKIN HAVING CROSS-CHANNELING

CROSS REFERENCE TO RELATED APPLICATIONS

This application is related to copending application Ser. No. 078,139, filed July 27, 1987, in the name of Promod Mavinkurve, entitled "Fluid Barrier Seal for Sanitary Napkins Having Undergarment Protecting Flaps", which is assigned to the assignee of this application and which is herein incorporated by reference.

1. Field of the Invention

This invention relates to protective, absorbent liners for undergarments, and more particularly, to improved sanitary protection for the transverse ends of napkins having undergarment protecting flaps.

2. Background of the Invention

Sanitary napkins have customarily included a central absorbent element having a body facing side, a garment facing side, longitudinally extending sides and transverse ends, In the past, these products sometimes failed to provide proper protection because the edges of the crotch of the panty, to which these products are adhered, tended to enfold onto the body facing side of the napkin. This condition can cause the panty to be stained with body fluid, either emanating from the napkin or exuding from the body of the wearer.

In order to overcome this deficiency, several of the more recent napkin designs have included flaps extending along the longitudinal sides of the absorbent element. Mattingly, U.S. Pat. No. 4,608,047, for example, is directed to such a sanitary napkin having flaps extending from a central absorbent. This product is adhesively attached to an inner crotch portion of a user's undergarment and its side flaps are then folded onto an outer surface of the crotch portion to protect the garment. McNair, U.S. Pat. No. 4,285,343, is also directed to a napkin having flaps for folding over the outer surface of the wearer's garment. Both of these patents provide for embodiments that include an absorbent tissue in their flaps, thereby inviting the transmission of body fluid from the central absorbent element. While sanitary napkins with wings or flaps have been designed to provide superior protection from fluid staining from the sides of the napkin, staining can often occur due to the transmission of body fluid from the transverse ends of these napkins. Accordingly, there is a need for limiting or delaying the transmission of fluid to the ends of these napkin designs so as to minimize "product failure".

In prior art sanitary napkins not having flaps extending laterally from their absorbent element, the techniques of indenting or compressing a portion of the central absorbent for assorted reasons has been suggested.

Matthews et al. U.S. Pat. No. 4,397,644, is directed to a sanitary napkin having an additional comfort layer disposed between the principle absorbent and the fluid permeable cover. This comfort component is integrated with the cover to provide intimate contact and densification to localized regions of the product. These densified regions create fluid transfer routes, whereby viscous body fluids can be directed into the principle absorbent. The densification of the additional absorbent component of Matthews, however, is designed for transferring, rather than delaying the transmission, of body fluid.

Mogor, U.S. Pat. No. 3,575,174, is directed to a sanitary napkin which is maintained in a shaped configuration by deep embossed channels impressed through the cover and into the core of the napkin to compression bond the two components together. The deep embossed channels are positioned near the lateral end edges on the top surface of the napkin and at the rearward end on the bottom surface of the napkin. The embossed channels are designed to shape the sanitary napkin for fit against the body of the wearer. This design is not intended to create delayed absorbency, nor is there a teaching for absorbent wings that provide protection by wrapping around the outer portion of the panty.

Joa, U.S. Pat. No. 2,721,554 is directed to a sanitary napkin having a pair of absorbent pads with a liquid-permeable tissue interposed between the pads for regulating the flow of liquid between the two absorbent elements. The patent teaches the use of a compression molding of the two pad elements near the transverse ends of the napkin for adhesion of the pads to each other through pressure knitting of their fibers at these localized zones. The invention further directs that one of the pads should be shorter than the other so that the thickness of the pad at its ends may be reduced without undue compression of the pulp. This patent, therefore, is not directed to delayed or compartmentalized absorbency, but rather, employs compressed areas of the pulp as a means for joining two pulp portions together.

Hirsch, U.S. Pat. No. 2,154,332 is directed to a sanitary utility pad having a petal construction with a pocket or depression for initially catching any fluid to be absorbed so that it will not run off the pad. The pocket of this invention appears to be a cut out of the central absorbent, rather than being a compressed portion of the pulp. The object of this device is to provide sufficient time for the filler or inner portion of the absorbent to absorb the body fluid before it runs off the fluid pervious surface. There is no teaching in this patent, however, for delayed absorbtion through the napkin by the extremities of the central absorbent.

Whitehead, U.S. Patent Des. Nos. 247,369, 247,370, 247,371, 247,372 are directed to ornamental designs for a contoured sanitary napkin, illustrating patterns embossed on the body-facing side of the napkin. These designs, however, do not appear to be directed to delayed absorbency and are primarily directed to aesthetic appearance.

German Patent No. 959,814, March 14, 1957, is directed to a diaper configuration with a notched central absorbent area having a water-tight cover on its body facing side and perforations in the bottom of the notched areas for transmitting fluid to the product's absorbent tissue.

While at least one of the above-mentioned patents, Hirsch, suggests preventing leakage of body fluid from the transverse ends of a sanitary napkin, none of these references is directed to sanitary napkins having panty-protecting flaps. Accordingly, if one were to compartmentalize the transverse ends of a central absorbent of a typical prior art napkin, body fluid would merely be directed to the longitudinal sides of the napkin which may have relatively little absorbing capacity, or none at all.

Accordingly, there is a need for a sanitary napkin, having absorbent flap portions, that provides a means for preventing the transmission of body fluid from its transverse ends. There is also a need for a compartmentalized sanitary napkin having reserve absorbent capacity on its transverse ends and longitudinal sides.

SUMMARY OF THE INVENTION

A sanitary napkin is provided having a fluid retarding means disposed transversely across its absorbent element for inhibiting the transmission of body fluid from a central portion of the absorbent element to one of the element's transverse ends. The design is especially suited to winged napkin configurations, especially those that have absorbent tissue in their flaps or wings. The preferred configuration for this invention includes two channels which are placed across the width of the absorbent pad such that the ends of each channel are within the portion of the napkin protected by the flaps. The channels preferably represent compressed portions of the absorbent element which allow the transmission of body fluid after a central portion of the absorbent element is saturated. This "delayed absorbency" represents an improvement, whereby a greater portion of the menstrual fluid is confined to the center of the winged sanitary napkin and the transverse ends of the napkin act predominantly as reserve capacity.

The densified or compressed pulp at each of the cross channels acts to retard the flow of fluid from the center portion of the absorbent element to the ends of the pad, where staining is often likely to occur. Because fluid is more adequately held in the center portion of the pad, due in part to the protection offered by the side flaps, the performance of the napkin is improved.

The channels of this invention also provide a better fitting napkin, since they rePresent a point at which the pad may be readily bent to conform to the body of the wearer. The ends of the preferred napkin can raise up with less resistance than a conventional napkin and, thus, provide a closer fit. This improved fit, particularly at the pad ends, leads to improved protection.

Thus, a winged sanitary napkin is provided having means for preventing the transmission of body fluid from its transverse ends. This napkin also provides for compartmentalized sanitary protection by including reserve absorbent capacity within the transverse ends as well as along the longitudinal sides of the central absorbent.

It is, therefore, an object of this invention to provide a winged sanitary napkin that provides improved protection from staining.

It is another object of this invention to provide a sanitary napkin that creates absorbent reserve areas at the transverse ends of the napkin that absorb body fluid after a central portion of the napkin has been saturated.

It is still another object of this invention to provide a sanitary napkin having multiple absorbent compartments designed to trap body fluid which is transferred along the body fluid pervious surface of the napkin.

With these and other objects in view, which will become apparent to one skilled in the art as the description proceeds, this invention resides in the novel construction, combination, arrangement of parts and methods substantially as hereinafter described and more particularly defined in the attached claims.

BRIEF DESCRIPTION OF THE DRAWINGS

The accompanying drawings illustrate a complete embodiment of the invention according to the best mode for the best practical application of the principles thereof, and in which:

FIG. 1: is a planar view of the body-facing side of a sanitary napkin embodiment of this invention illustrating the fluid retarding channels disposed across the absorbent element;

FIG. 2: is a planar view of the sanitary napkin embodiment of FIG. 1 illustrating the undergarment-facing side and adhesive strips;

FIG. 3: is a partial, transverse, cross-sectional view of the napkin of FIG. 1, taken through line 3—3, illustrating the fluid retarding channel of this embodiment.

FIG. 4: is a transverse, cross-sectional view of an alternative fluid retarding means comprising a treated portion of the central absorbent element.

DESCRIPTION OF THE INVENTION

Figure 5:
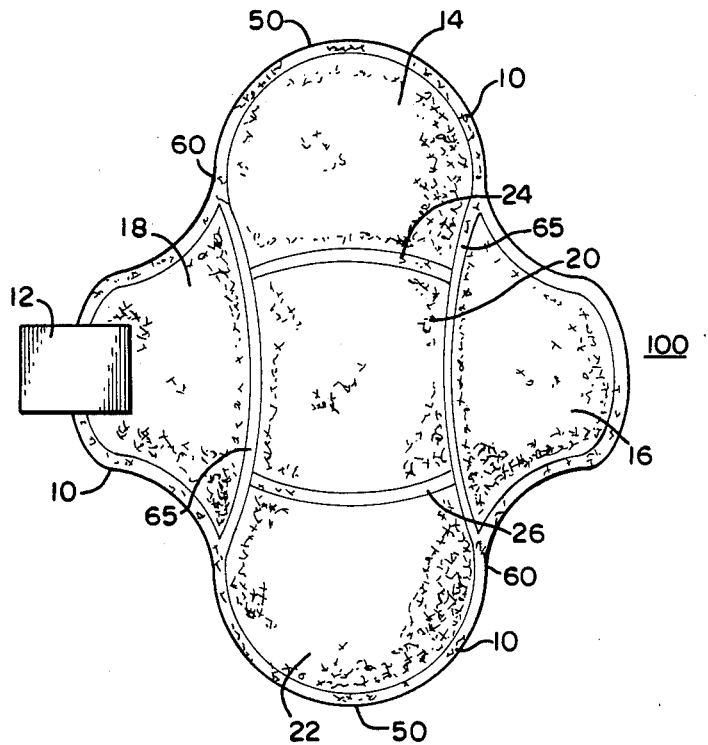
FIG. 5: is a planar view of the body-facing side of an alternative preferred sanitary napkin embodiment illustrating a fluid barrier seal means disposed between the flaps and the absorbent element of the napkin.

In accordance with the teachings of this invention, an improved sanitary napkin is provided for minimizing panty staining due to leakage from the napkins transverse ends. The sanitary napkin of this invention includes an absorbent element and flaps extending laterally from this element. An important feature of the napkin is a fluid retarding means disposed transversely across the absorbent pad for inhibiting the transmission of body fluid from a central portion of the pad to one of the transverse ends of the napkin. The invention is designed to improve the performance of a preferred winged sanitary napkin by minimizing the potential for failure at the transverse ends.

Referring now to FIGS. 1-3, which illustrate in planar and cross-sectional views, a preferred sanitary napkin 100. embodying the teachings of this invention. The sanitary napkin 100 comprises an absorbent element having longitudinally extending sides 60 and transverse ends 50. The napkin 100 further includes flaps 16 and 18 extending laterally from each of the longitudinal sides 60 of the absorbent element. An important aspect of this invention is a fluid retarding means which is disposed transversely across the absorbent element for inhibiting the transmission of body fluid from a central portion 20 of the absorbent element to one of the transverse ends 50. The fluid retarding means of this invention preferably comprises at least two compressed channels 24 and 26 of the absorbent element. In a preferred embodiment, flaps 16 and 18 comprise absorbent material, such as an absorbent tissue, enabling the flaps 16 and 18 to also absorb body fluid which may be transferred from the central portion 20 of the absorbent element.

Generally the compressed portions 24 and 26 of the napkin 100 are designed to divide the absorbent element into central component 20 and two end components 14 and 22. The central component 20, as illustrated in FIG. 1, preferably has a larger surface area than the end components 14 and 22. It is also desirable that the preferred compressed portions be disposed along curvilinear paths as shown by FIG. 1. Although this construction is not a requirement, it maximizes the area of the central component 20 while permitting lateral transfer of fluid from the absorbent element into the flaps 16 and 18.

Although the fluid retarding means preferably comprises mechanically compressed portions of the pulp of the central absorbent element, body fluid transfer could also be inhibited by chemically treating the pulp with standard repellant materials, as illustrated by FIG. 4.

These may include, for example, emulsions of fluorocarbon polymers, wax or silicone polymers.

This invention contemplates, as a preferred embodiment, employing a fluid barrier seal 65 and compressed areas 24 and 26 of the napkin for regulating the flow of body fluid from the central portion 20 of the napkin 100. AS used herein, a "fluid barrier seal" refers to any sealing means which will prevent body fluid from transferring either by wicking or seeping across the seal. In one preferred embodiment, as depicted in FIG. 5, the napkin 100 comprises body fluid sealing means 65 disposed between the absorbent element and the flaps 16 and 18 for preventing the transmission of body fluid from the absorbent element across the flaps 16 and 18. In such a design, the flaps 16 and 18 would preferentially be used only as backup compartments to absorb fluid from occasional gushing, fluid that could have been smeared to the body, or fluid exuding from leaky, misplaced napkins. When combined with the novel channels of this invention, the flaps 16 and 18, including a body fluid barrier seal 65, would minimize the incidence of napkin failure through the longitudinal sides 60, and would concentrate the body fluid within the central portion 20 of the absorbent area. Accordingly, this would direct the flow of body fluid into the two end components 14 and 22 at an earlier time than without a seal 65.

Without the fluid barrier seal 65 between the central absorbent 20 and the flaps 16 and 18, body fluids travel through the central absorbent element and into the bottom tissue of the napkin. This bottom tissue often includes fine capillaries that enable the body fluid the travel at a faster rate and spread through the tissue into the flaps 16 and 18. In such a design, a molded pulp within the central portion 20 of the absorbent element and the tissue within the flap portions 16 and 18 become one absorbent system. The end components 14 and 22 would then be available to accept the overflow of body fluid from this one absorbent system.

When fluid seal 65 is provided, it is preferrably disposed along the entire boundary between the absorbent element and the flaps 16 and 18. In addition to this sealing means 65, the sanitary napkin 100 may further comprise a fluid tight seal 10 around the entire periphery of the napkin 100, including the flaps 16 and 8. The flaps 16 and 18 are preferably sealed around their perimeter, and generally can be selected to comprise a width that is greater than the adjoining length of the central compartment 20. As used herein, the "width" of the flaps 16 and 18 refers to the dimension of the flaps 16 and 18 that borders the absorbent element of the napkin 100.

The preferred compressed portions 24 and 26 of the napkin 100. representing the fluid retarding means of this invention, preferably have end points which lie on a pair of junction lines between the absorbent element and the flaps 16 and 18. Body fluid absorbed by the central component 20 of this embodiment is transmitted into the flaps 16 and 18 in the absence of a fluid barrier seal 65.

It is further anticipated that the sanitary napkin 100 can be folded along the compressed portions 24 and 26 to provide a better fit for the napkin, preferably to provide a concave configuration for the body side surface of the napkin 100. This "better fit" capability is provided because the channels or compressed areas 24 and 26 provide a point at which the napkin 100 may be readily bent. The compressed areas 24 and 26 provide hinges so that the ends of the napkin can raise up with less resistance, enabling the napkin to fit snug against the body, which corresponds generally to improved protection.

The absorbent element of this invention should be made of soft, comfortable material. Preferably this element is cut into an "hour glass shape" as illustrated in FIGS. 1 and 2. Adequate absorbency may be built into the core of the absorbent without adding bulk by adding superabsorbent materials, now known, which have the properties of high-liquid retention, for example, crosslinked acrylate polymers. The absorbent element should retain fluid well without allowing it to squeeze out and re-wet the wearer.

Generally, the absorbent element should be about 4–10 inches in length, preferably about 6–9 inches. As described in FIG. 3, the absorbent element comprises a core 100 which preferably is made of loosely associated absorbent hydrophilic materials such as cellulose fibers, wood pulp, regenerated cellulose or cotton fiber, and/or other materials generally known in the art. Such fibers may be chemically or physically modified and the core may include such fibers in combination with other materials, both natural and synthetic, such as hydrophilic foams, hydrophilic polymers, or the like. However, for the preferred embodiment of this invention, wood pulp is the material of choice because of its availability and inexpensive cost.

As is customary in the art, covering the side of the napkin to be worn against the body of the user, is a body fluid pervious surface 42. The body fluid pervious surface 42 can be a resilient, relatively non-absorbing, fluid pervious material. This material is provided for comfort and conformability and directs fluid to an underlying layer, for example, wood pulp, which retains such fluid. This surface 42 may be woven or non-woven material pervious to body fluid contacting its surface. The body-facing material should be soft and easily permeated by body fluids. Preferably, this surface 42 should be made of a material which allows the passage of fluid without moving it appreciably in its horizontal plane. Furthermore, it should retain little or no fluid in its structure to provide a relatively dry surface next to the skin. Generally, the fluid permeable surface 42 is a single, rectangular sheet of material having a width sufficient to cover the body-facing side of the absorbent element. Preferably the fluid pervious surface 42 is longer than the core 46 so as to form end tabs, which may be sealed with another pervious or non-pervious layer to fully enclose the core 46. The fluid pervious surface 42 is preferably made of fibers or filaments of thermoplastic polymers such as polyethylene or polypropylene.

Underlying the core 46 of the absorbent element can be another layer of absorbent material (not shown) to provide additional resiliency to the product. This additional layer can extend beyond the longitudinal sides 60 of the absorbent core 46 to entrap any body fluid which escapes from the side of the absorbent element. This layer may be substantially wider than the core 46 of the central absorbent and, may extend into the flaps 16 and 18. The absorbent layer may comprise a thin, absorbent layer of material such as a tissue, fabric or the like, made of cellulosic fibers. Because such material is provided as a safety measure and is only required to contain escaped fluid, it need not be very absorbent at all and, in fact, may be comprised of any capillary or cellular system including hydrophobic material. However, the preferred material is a hydrophilic fabric comprised of celluosic fibers such as wood pulp tissue or other suitable hydrophilic woven or nonwoven material. It should also be understood that while such materials preferably extend into the flaps 16 and 18 for the full distance from the absorbent element, if desired, this absorbent tissue may extend only a short distance from absorbent element.

The sanitary napkin 100 of this invention further includes a body fluid impervious surface 44 on the undergarment-facing side of the absorbent element. The impervious surface way allows passage of air and moisture vapor while substantially blocking the passage of fluid to the outer surface. The impervious surface 44 may be heat sealed or fastened by way of adhesives to the core 46 or to the core 46 wrapped in a pervious surface cover and preferrably extends over wing areas 16 and 18. The impervious surface 44 may comprise any thin, flexible, body fluid impermeable material such as, a polymeric film, for example, polyethylene, polypropylene, cellophane or even a normally fluid pervious material that has been treated to be impervious such as impregnated fluid repellent paper or nonwoven fabric.

The absorbent tissue can be heat sealed or adhesively sealed around the edges of the flaps 16 and 18 with the preferred impervious backings and body fluid pervious covers of the flaps to form compartmentalized absorbing areas.

Referring now to FIG. 2, the attachment adhesive elements of this invention can be made of any known pressure-sensitive adhesive material. As used herein, the term "pressure-sensitive" refers to any releasable adhesive or releasable tenacious means. Adhesive compositions suitable for sanitary napkins include, for example, the water-based pressure-sensitive adhesives such as acrylate adhesives, e.g. vinyl acetate-2 ethyl hexyl acetate copolymer which is generally combined with tackifiers such as, for example, ethylene amine. Alternatively, the adhesive may comprise the rapid setting thermoplastic "hot melt" adhesives. The adhesive elements may also comprise a two-sided adhesive tape. It is also anticipated that adhesives based on an elastomer selected from natural or synthetic rubbers could be used. Several adhesive placements are deemed adequate for adhering the preferred napkin 100 to an undergarment and for securing the flaps. See Mattingly, U.S. Pat. No. 4,608,047 and McNair, U.S. Pat. No. 4,285,343, which teachings are herein incorporated by reference. It will be understood that alternative shapes for these adhesives, for examples, lines, squares, circles, etc., may also be employed.

FIG. 2 illustrates an embodiment having an adhesive element 37 with release strip 12 affixed to flap 18 of the napkin. The adhesive strip 37 is the means for fixing the flaps 16 and 18 to the outer crotch portion of the undergarment. In this embodiment, the flaps overlap each other as they overlay the outer crotch portion of the undergarment and the adhesive element 37 is so placed as to be in an area of the overlap. The adhesive element 37 serves to hold the napkin in place by adhering one flap to the other.

Alternatively, each of the flaps 16 and 18 may have adhesive means disposed on their surfaces for attaching the napkin 100 to the inner crotch portion of an undergarment. See McNair, U.S. Pat. No. 4,285,343. In this embodiment, the flaps are folded upon an outer portion of the undergarment and secured using their own pressure-sensitive adhesive means. The napkin may also employ adhesive 35 lines for attaching the central absorbent to the inner crotch portion of the undergarment.

From the foregoing it can be realized that this invention provides a improved winged sanitary napkin having a central absorbent component and end components that have delayed action absorbency. This is a unique improvement over the current state of the art napkins having flaps and a single central absorbent pad, since failure through the transverse ends of the napkin can be minimized. Although various embodiments have been illustrated, this was for the purpose of describing, but not limiting the invention. Various modifications, which will become apparent to one skilled in the art, are within the scope of this invention described in the attached claims.

What is claimed is:

1. A sanitary napkin comprising:
   (a) an absorbent element having longitudinally extending sides and transverse ends;
   (b) flaps extending laterally from each of said longitudinally extending sides of said absorbent element; and
   (c) a fluid retarding means disposed transversely across said element for inhibiting the transmission of body fluid from a central portion of said absorbent element to one of said transverse ends of said absorbent element.

2. The sanitary napkin of claim 1 wherein said fluid retarding means comprises at least two compressed portions of said absorbent element, which defining a central portion and inhibiting the transmission of body fluid from said central portion of said absorbent element to each of said transverse ends.

3. The sanitary napkin of claim 2 wherein said flaps comprise absorbent material.

4. The sanitary napkin of claim 2 wherein said compressed portions are disposed along curvilinear paths, said paths having ends disposed on the longitudinally extending sides of said absorbent element.

5. The sanitary napkin of claim 3 further comprising body fluid sealing means disposed between said absorbent element and said flaps for preventing the transmission of body fluid from said absorbent element into said flaps.

6. The sanitary napkin of claim 5 wherein said body fluid sealing means is disposed along the entire boundary between said absorbent element and said flaps.

7. The sanitary napkin of claim 3 further comprising fluid tight seal means around the entire periphery of said sanitary napkin.

8. The sanitary napkin of claim 3 wherein said compressed portions have end points which lie on a pair of junction lines located between said absorbent element and said flaps.

9. The sanitary napkin of claim 8 wherein said flaps comprise a width that is greater than the length of said central portion of the absorbent element.

10. The sanitarY napkin of claim 2 wherein said napkin is folded along the compressed portions of the absorbent element to provide a better fit for said napkin.

11. The napkin of claim 10 wherein said absorbent element is folded along said compressed portions to provide a concave configuration for a body side surface of said napkin.

12. A sanitary napkin comprising:
   (a) an absorbent element having longitudinally extending sides and transverse ends, and comprising an absorbent core, a liquid impermeable cover on one side of said absorbent core and a liquid impermeable barrier on the other side of said absorbent core;

(b) flaps comprising said cover and said barrier extending laterally from each of said absorbent element, and (c) fluid retarding means disposed transversely across said absorbent element for inhibiting the transmission of body fluids from a central portion of said absorbent element to one of said transverse ends.

13. The sanitary napkin of claim 12 wherein said fluid retarding means comprises a compressed portion of said absorbent element defining a channel therein.

14. The sanitary napkin of claim 13 wherein said fluid retarding means comprises a pair of spaced apart channels defining a central portion and two end portions of said absorbent element.

15. The sanitary napkin of claim 12 comprising a further absorbent material disposed between said absorbent core and said barrier and extending into said flaps between said cover and said barrier.

16. The sanitary nakin of claim 15 comprising body fluid sealing means disposed between said absorbent element and said flaps for preventing the transmission of body fluids from said absorbent element into said flaps.

17. The sanitary napkin of claim 13 wherein said fluid retarding means comprises a portion of said absorbent core treated with a fluid repellent composition.

18. The sanitary napkin of claim 13 wherein said fluid retarding means are disposed on either side of the central portion of said absorbent element and extend between said flaps to define a central absorbent portion and two end portions of said absorbent element.

19. The sanitary napkin of claim 18 wherein said fluid retarding means are disposed along curvilinear paths to define a central absorbent portion having convex transverse ends.

20. The sanitary napkin of claim 19 wherein said absorbent element is hour-glass shaped and said central absorbent portion has concave longitudinal sides.

* * * * *